United States Patent [19]

Ito et al.

[11] Patent Number: 4,467,214
[45] Date of Patent: Aug. 21, 1984

[54] METHOD OF AND APPARATUS FOR DETECTING EXTERNAL DEFECTS OF A CIRCULAR SEALING MEMBER

[75] Inventors: Hiroshi Ito, Nagoya; Hiroshi Kuno, Toyota; Tooru Kai, Inazawa, all of Japan

[73] Assignees: Kabushiki Kaisha Toyota Chuo Kenkyusho; Toyoda Gosei Co., Ltd., both of Aichi, Japan

[21] Appl. No.: 272,360

[22] Filed: Jun. 10, 1981

[30] Foreign Application Priority Data

Jun. 13, 1980 [JP] Japan ................................. 55-79835

[51] Int. Cl.³ .......................................... G01N 21/88
[52] U.S. Cl. .................................... 250/563; 356/237
[58] Field of Search ............... 250/223 B, 223 R, 572, 250/561, 562, 563; 209/526; 356/240, 428, 237

[56] References Cited

U.S. PATENT DOCUMENTS 3,340,400  9/1967  Quittner ............................. 250/562
4,066,363  1/1978  Juvinall ............................. 356/198
4,136,779  1/1979  Bieringer .......................... 209/524
4,160,913  7/1979  Brenholdt ......................... 250/563

Primary Examiner—David C. Nelms
Assistant Examiner—J. Brophy
Attorney, Agent, or Firm—Koda and Androlia

[57] ABSTRACT

A method and apparatus for detecting external defects of a circular sealing member by means of irradiation of detecting rays. A laser detecting ray for scanning is irradiated to a surface of the circular member which is rotated at the detecting section, and reflected light from the surface is received to be converted into electric signals so that the surface defects can be optically inspected. In case there is a defective surface, an irregularly reflected light can be received and based on an extracted signal a defective surface can be easily discriminated from the normal surface. The circular member is delivered one after another to the detecting section wherein discrimination is automatically made whether the circular member is non-defective or defective by means of rotation, irradiation of detecting rays and defect detecting action.

14 Claims, 20 Drawing Figures

METHOD OF AND APPARATUS FOR DETECTING EXTERNAL DEFECTS OF A CIRCULAR SEALING MEMBER

BACKGROUND OF THE INVENTION

1. Field of the Invention

The present invention relates to a method of and apparatus for detecting external defects of a circular sealing member, and in particular to a method of and apparatus for detecting external defects which can be automatically and optically detected without touching thereon.

2. Description of the Prior Art

In various industrial fields, the circular members are widely used for the purpose of hermetic sealing and the like, and elastomeric materials such as rubber, plastics, etc. are selected therefor. The circular member of the type described includes a sealing portion, and the defects in this sealing portion tend to cause serious problems. In this connection, heretofore, necessity has been voiced for a system for detecting the defects in the sealing portions with high precision.

As well known, various types of seal members are used in oil or water pressure apparatuses, for example, and, particularly, the circular seal member being of a circular shape or a cup shape is provided on a piston slidable in a cylinder. The circular seal member of this type forms the most important functional part for the transmission of pressure. The sealing surface of the circular seal member, therefore, must be finished with high accuracy and be thoroughly inspected in its material quality before being disposed in the apparatus since the external defects of the circular seal member causes a pressure leakage, lowered durability, breakage and the like.

It is also well known that a rubber cup is used in the brake cylinder for use in an automobile, etc. as the circular seal member, which is such an important functional part that the depressed force applied onto the brake pedal by a driver is converted into an oil pressure force to apply a braking force to the wheels. Since the lowered quality of the cup seal of this type renders an adverse influence on braking functions of the automobile, satisfactory quality and high durability are required. Accordingly, the cup seals of the automobile, etc. must be inspected in its total number before being assembled into brake cylinders of the automobile to positively detect external defects even if the defects are very small, thus rejecting such cups as the defective ones.

The detection of defects in the circular seal member has heretofore been performed by visual inspection, and many inspectors have been required for the visual inspection of all the products of the cup seals as described above. The visual inspection also has such drawbacks that personal error and extent of fatigue of the individual inspectors tend to result in a scattering in the result of the inspection to a considerable extent, and further, that a large number of seal members cannot be automatically and effectively inspected.

A plurality of seal members such as the cup seals as described above are shaped from one rubber sheet at the same time in ordinary cases, and in the subsequent step, each cup is detached from the sheet to become a single product. In this detaching step the cutting blade is pressed against a given portion, and the roughness of the cutting blade in the cutting surface, the shifting movement of rubber sheet during cutting, etc. tend to cause flaws on the planer surface constituting a surface being finished. This planer surface does not make direct sliding contact with a brake cylinder, etc. but external defects such as surface roughening, burrs, pin holes, cracks, cuts, etc. cause considerably lowered durability of cup seal, and these external defects to extend over all the sealing portion in a short time use. The defects on such planer surface are caused by wear and damages of the cutting blade in many cases, and therefore, it is preferable that the planer surface inspection of the circular seal member is performed upon the completion of the detaching step. As seen in the conventional production, in case of inspection of the stored seal members in the final step, such a problem has been presented that it is not until a large number of defective seal members are produced that an abnormality of the cutting blade is found. Necessity has heretofore been voiced for the provision of the inspection step immediately after the finishing step. However, the above described visual inspection has presented such a disadvantage that the provision of the inspection step immediately after the detaching step has not been practicable because of the safety control for the inspectors and other factors.

SUMMARY OF THE INVENTION

The present invention has been developed to obviate the above described disadvantages of the prior art and has as its object the provision of a detecting method and means by which external defects of a circular sealing member can be automatically and optically inspected in a stabilized condition without touching thereon immediately after the detaching step.

In keeping with the principles of the present invention, the object is accomplished with a first detecting method in accordance with the teachings of the present invention in which the circular members are delivered one after another to an inspection section in a predetermined posture, a detecting ray for scanning is irradiated to a conical surface of the circular member which is rotated in the inspection section after being delivered, a regularly reflected light from the conical surface of the circular member is received to be converted into electrical signals, and the electrical signals are electrically processed and extract therefrom a signal corresponding to a defect on the conical surface, whereby determination is made whether the conical surface is non-defective or defective based on said extracted signal, thereby offering such a characteristic feature that continuous selection can be performed.

The object is also accomplished with a second detecting method in accordance with the teachings of the present invention in which the circular members are delivered one after another to the inspection section in a predetermined posture, a slit light flux is irradiated at an incidence angle large enough to cause regular (or specular) light reflection to an upper surface of the circular member which is rotated in the inspection section after being delivered, a regularly reflected light from the upper surface of the circular member is received to be converted into electric signals, and the electric signals are electrically processed to extract therefrom a signal corresponding to a defect on the upper surface, whereby determination is made whether the upper surface is non-defective or defective based on said extracted signal, thereby offering such a characteristic feature that continuous selection can be performed.

The object is also accomplished with a third method in accordance with the teachings of the present invention in which the circular members are delivered one after another to the inspection section in a predetermined posture, a slit light flux is irradiated to a radially outwardly projected portion of the circular member in the direction of the axis of the circular member, the circular member being rotated in the inspection section after being delivered, the light not interrupted by the projected portion is received to be converted into electric signals, and the electric signals are electrically processed and extract therefrom a signal corresponding to a defect on the projected portion, whereby determination is made whether the projected portion is non-defective or defective based on said extracted signal, thereby offering such a characteristic feature that continuous selection can be performed.

The object is further accomplished with a fourth method in accordance with the teachings of the present invention in which the circular members are delivered one after another to the inspection section in a predetermined posture, detecting rays for scanning are irradiated to the conical surface of the circular member, a slit light flux to the upper surface at a large incidence angle, and further, a slit light flux to the projected portion, respectively, the regularly reflected light from the conical surface and the upper surface and the light not interrupted by the projected portion are received to be converted into electric signals, the electric signals are electrically processed to extract therefrom signals corresponding to the external defects, whereby determination is made whether the circular member is non-defective or defective based on said extracted signal, thereby offering such a characteristic feature that continuous selection can be performed.

Furthermore, in keeping with the principles of the present invention, the object of the present invention is accomplished with a first detecting means including a rotary stand which is rotatably mounted on a detecting table and placed thereon with a circular member, an automatic delivering mechanism which delivers the circular members to be inspected one after another to the rotary stand in a predetermined posture, a scanning light source for irradiating detecting rays, which are controlled and scanned at a speed faster than the rotating speed of the rotary stand substantially in parallel with the rotary axis of the rotary stand, to the conical surface of the circular member, a photoelectric detector for receiving a regularly reflected light from the conical surface to convert same into electric signals, a defect detecting circuit for continuously processing the electric signals of the photoelectric detector at least per full rotation of the rotary stand and detecting the external defects of the circular member, and a selecting mechanism for selecting non-defective circular members from defective ones upon completion of the inspection in response to the defect detecting signals of the defect detecting circuit, thereby offering such a characteristic feature that the external defects can be automatically and optically detected without touching the circular member.

The object of the present invention is also accomplished with a second detecting means including a rotary stand which is rotatably mounted on a detecting table placed thereon with a circular member to be rotated, an automatic delivery mechanism for delivering circular members to be inspected one after another to the rotary stand in a predetermined posture, a slit light flux generating device for irradiating a slit light flux traversing the upper surface of the circular member at an incidence angle large enough to cause regular light reflection, a photoelectric detector for receiving a regularly reflected light from the upper surface to convert same into electric signals, a defect detecting circuit for continuously processing the electric signals of the photoelectric detector at least per full rotation of the rotary stand and detecting the external defects of the circular member, and a selecting mechanism for selecting non-defective circular members from defective ones upon completion of the inspection in accordance with the defect detecting signals of the defect detecting circuit, thereby offering such a characteristic feature that the external defects can be automatically and optically inspected without touching the circular member.

The object of the present invention is also accomplished with a third detecting means including a rotary stand which is rotatably mounted on a detecting table and placed thereon with a circular member to be rotated, an automatic delivery mechanism for delivering circular members to be inspected one after another to the rotary stand in a predetermined posture, a slit light flux generating device for irradiating a slit light flux to a radially outwardly projected portion of the circular member in the direction of the axis of the circular member, a photoelectric detecting array for receiving the light not interrupted by the projected portion to convert same into electric signals, a projection detecting circuit for detecting a defect in the projected portion in accordance with the received light in response to an output of the photoelectric detecting array, a defect detecting circuit for continuously processing the electric signals of the projection detecting circuit at least per full rotation of the rotary stand and detecting the external defects of the circular member, and a selecting mechanism for selecting non-defective circular members from defective ones upon completion of the inspection in response to defect detecting signals of the defect detecting circuit, thereby offering such a characteristic feature that the external defects can be automatically and optically inspected without touching the circular member.

The object of the present invention is further accomplished with a fourth detecting means including a rotary stand which is rotatably mounted on a detecting table and placed thereon with a circular member, an automatic delivery mechanism for delivering circular members to be inspected one after another to the rotary stand in a predetermined posture, a scanning light source for irradiating detecting rays, which are controlled and scanned at a speed faster than rotating speed of the rotary stand substantially in parallel with the rotary axis of the rotary stand, to the conical surface of the circular member, a slit light flux generating device for irradiating a slit light flux to a radially outwardly projected portion of the circular member in the direction of the axis thereof as well as irradiating a slit light flux traversing the upper surface of the circular member at a large incidence angle, a first photoelectric detector for receiving a regularly reflected light from the conical surface to convert same into electric signals, a photoelectric detecting array for receiving the transmitted light from the projection portion to convert same into electric signals, a projection detecting circuit for detecting a defect on the projected portion in accordance with the received light in response to an output of the photoelectric detecting array, a second photoelectric detector for receiving a regularly reflected light from the upper surface to convert same into electric signals, a defect detecting circuit for continuously processing the electric signals of the first photoelectric detector, the projection detecting circuit and the second photoelectric detector at least per full rotation of the rotary stand and detecting the external defects of the circular member, and a selecting mechanism for selecting non-defective circular members from defective ones upon completion of the inspection in response to defect detecting signals of the defect detecting circuit, thereby offering such a characteristic feature that the external defects can be automatically and optically inspected without touching the circular member.

BRIEF DESCRIPTION OF DRAWINGS

The above mentioned features and object of the present invention will become more apparent by reference to the following description in conjunction with the accompanying drawings, wherein like reference numerals denote like elements, in which.

DETAILED DESCRIPTION OF THE INVENTION

Figure 1:
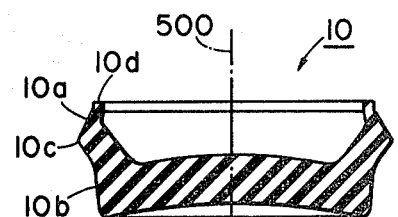
FIG. 1 is a sectional view of a preferred example of the circular seal member to be inspected in accordance with the teachings of the present invention.

Referring more particularly to the drawings, shown in FIG. 1 is an automobile cup seal as a preferred example of the circular member in the present invention to be inspected whether or not there are external defects. This circular seal member 10 is made from soft rubber and symmetric with respect to an axis 500. This circular seal member is inserted into an automobile brake cylinder and its outer peripheral surface functions as a sealing surface. The circular seal member 10 in FIG. 1 has four important sealing portions, that is, conical surfaces 10a and 10b which are frustums of cone brought into contact with the cylinder, a radially outwardly projected portion 10c which forms a bordering ridge between the both conical or upper surfaces 10a and 10b, and a planer surface 10d which is a circular finished face forming the top surface of the circular seal member 10. Described in an embodiment hereunder will be a means by which external defects are detected at the same time at the respective portions of the conical surfaces 10a and 10b, the projected portion 10c and the planer surface 10d.

Figure 2:
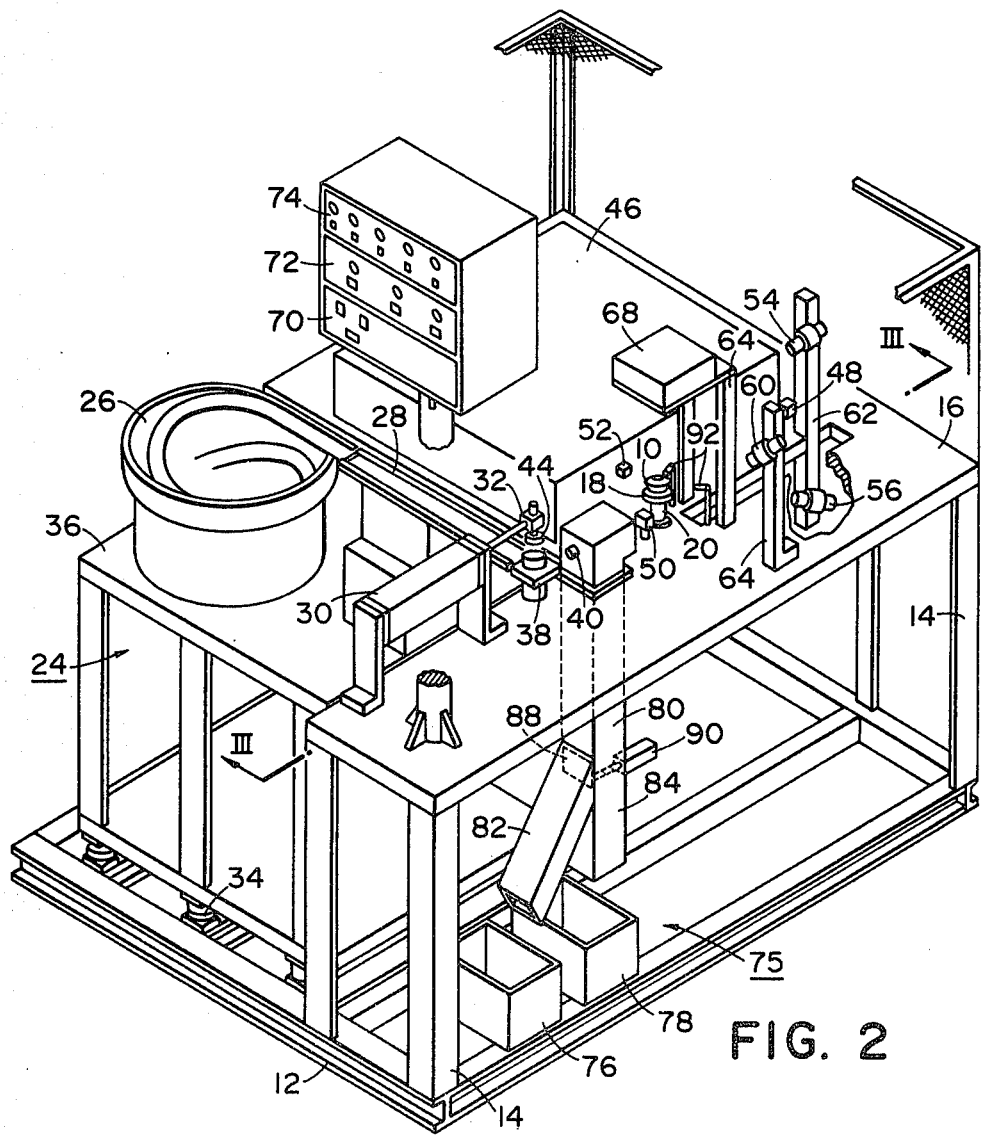
FIG. 2 is a perspective view showing a preferred embodiment of an external defect detecting means in accordance with the teachings of the present invention.
Figure 3:
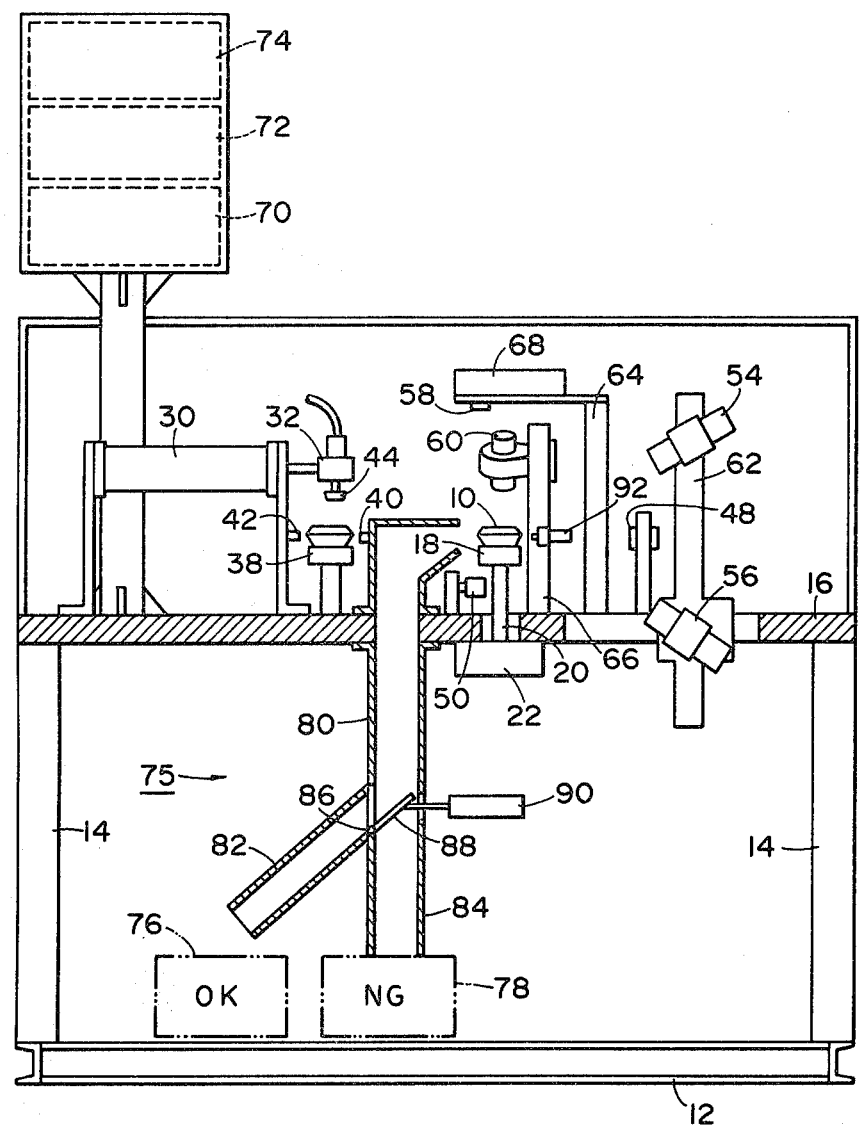
FIG. 3 is a sectional view taken on the line III—III of FIG. 2.

FIG. 2 shows a general composition of the external defects detecting means in accordance with the teachings of the present invention and its sectional view is shown in FIG. 3. Fixed to a base 12 through a plurality of supports 14 is a detecting table 16 and a rotary stand 18 is rotatably mounted on the detecting table 16 so that the circular seal member 10 shown in FIG. 1 can be placed rotatably on the rotary stand 18. A rotary stand shaft 20 of the rotary stand 18 is connected to a rotary mechanism 22 which is fixed to the undersurface of the detecting table 16, and the rotary stand 18 of the circular seal member 10 is rotated at a constant speed by a motor provided in the rotary mechanism 22 to be described hereinafter.

In order to deliver the circular seal member 10 to be inspected to the above mentioned rotary stand 18 one after another in a predetermined posture immediately after the detaching step, an automatic delivery mechanism 24 is provided. The automatic delivery mechanism 24 includes an orienting feeder 26, a straightening feeder 28, a conveying cylinder 30 and an attracting cylinder 32, and delivers the circular seal members 10 automatically. The orienting feeder 26 and the straightening feeder 28 are fixed to a feeder base board 36 which is supported on the base 12 via anti-vibration rubbers. Both of the feeders 26 and 28 are given predetermined mechanical minute vibrations by a vibrating source, not shown, to have the plurality of circular seal members 10 move forward in the orienting feeder 26 one after another in a posture under a given orientation to the straightening feeder 28. Provided at the output end of the straightening feeder 28 is a stock stand 38 which is fixed to the detecting table 16, and the circular seal members 10 delivered through the straightening feeder 28 once stops on the stock stand 38. A pair of photoelectric sensors 40 and 42 check the presence of the circular seal member 10 placed on the stock stand 38. In case the presence of the circular seal member 10 is checked on the stock stand 38, an attracting head 44 provided at the forward end of an attracting cylinder 32 moves down toward the circular seal member 10 to attract the circular seal member 10 by the attracting head 44 by air suction, and is moved upward by the attracting cylinder 32. Then next circular seal member 10 is delivered through the straightening feeder 28 to the stock stand 38, and stays there being ready for the next inspection. The circular seal member 10 attracted and moved upward by the attracting head 44 is moved above the rotary stand 18 by a forwarding action of the conveying cylinder 30, and placed through the downward action of the attracting cylinder 32 and the action of the attracting head 44.

As mentioned hereinabove, the circular seal member 10 to be inspected is correctly delivered to the rotary stand by the automatic delivery mechanism 24, and the attracting cylinder 32 is returned to the original position by the conveying cylinder 30 to get ready for the next delivery action. In addition, any delivery mechanism may be adopted only if it can place the circular seal member 10 to be inspected on the rotary stand 18.

When the circular seal member 10 is placed on the rotary stand 18, the rotary stand 18 is driven to be rotated at a predetermined speed by the rotary mechanism 22, and, at the same time, detecting rays are irradiated from a polarizing scanning light source and a slit light flux generating device mounted in an optical system unit 46 to the conical surfaces 10a and 10b, the projected portion 10c and the planer surface 10d so that the optical external defect inspection is started without mechanically touching the circular seal member. More specifically, conical surface inspecting rays controlled and scanned at a speed faster than the rotating speed of the rotary stand 18 are irradiated through a projector lens 48 to the conical surfaces 10a and 10b of the circular seal member 10 substantially in parallel to the rotary axis of the rotary stand, and projected portion inspecting slit light flux is irradiated from a projector mirror 50 of the slit light flux generating device to the projected portion 10c of the circular seal member 10. Furthermore, a planer surface inspecting slit light flux traversing the planer surface 10d is irradiated at a large incidence angle from a slit section 52 of the slit light flux generating device to the planer surface 10d of the circular seal member 10.

According to the present invention, as described above, each of the surfaces of the rotating circular seal member 10 is irradiated by the inspecting rays, and the optical external defects inspection is performed by receipt of the reflected light from each of the surfaces. In order to do this, mounted therein are first photoelectric detectors 54 and 56 which receive the regularly reflected lights from the conical surfaces 10a and 10b to convert same into electric signals, photoelectric detecting array 58 which receives the light transmitted through the projected portion 10c to convert same into electric signals, and a second photoelectric detector 60 which receives the regularly reflected light from the planer surface 10d to convert same into electric signals. In the embodiment, each of the above mentioned detectors 54 and 56, detecting array 58 and detector 60 are respectively solidly secured to the supports 62, 64 and 66 which in turn are fixed to the detecting table 16. Incidentally, irradiating means of inspecting lights to each of the surfaces and the means for receiving and detecting the reflected and transmitted lights may be utilized in either a single or combined state, and may be fixed either to a single detecting table or to a plurality of detecting tables separately.

Connected to the above mentioned photoelectric detecting array 58 is a projection detecting circuit 68 which detects the projected portion 10c by the transmitted light in response to an output from the photoelectric detecting array 58. In the drawing, the projection detecting circuit 68 is provided in the circuit unit fixed to the support 64.

The electric signals emitted in response to the reflected lights which are detected by each of the above mentioned photoelectric detectors are continuously processed per full rotation of the rotary stand 18 and detect external defects of the circular seal member 10 in a defect detecting circuit. In the embodiment, the defect detecting circuit includes a microcomputer 70 and an interface 72 and performs automatic defect detection by aggregation and operation of data fed from each of inspecting systems.

The result of the determination by the above mentioned microcomputer 70 and interface 72 is indicated by a lamp or the like at an indication section 74 and determination signals are supplied to a selecting mechanism which will be described hereinunder to, make selection of the circular seal members 10, which have been inspected.

The above mentioned indication section 74 indicates "OK" or "NG" based on the results, and is provided with a counter for counting the number of the lamps lighted to show the rejection rate of the circular seal members being continuously inspected.

The selecting mechanism 75 includes a non-defective article container 76 and a defective article container 78 which are provided downwardly of the detecting table 16 and on the base 12. An ejecting duct 80 open in the vicinity of the rotary stand 18 and its outlets are led to the above mentioned non-defective article container 76 and defective article container 78 by way of a non-defective article duct 82 and a defective article duct 84, respectively. At the diverging point of both ducts 82 and 84, a damper 88 is swingably supported by a shaft 86 and the operation of the damper 88 is controlled by a determining cylinder 90. In other words, when the microcomputor 70 determines a non-defective article, the determining cylinder 90 controls to operate the damper 88 as shown in FIG. 3 to convert the ejecting duct 80 to the non-defective article duct 82 and the non-defective circular seal member 10 is ejected to the non-defective article container 76. On the other hand, in case of the determination of a defective article, the determining cylinder 90 turns the damper 88 in the counter-clockwise direction to connect the ejecting duct 80 to the defective article duct 84 to eject the defective circular seal member 10 to the defective article container 78. Operation of the determining cylinder 90 is performed at the same time as the indicating action of the indication section 74 and the inspected circular seal member 10 is blown forward into the ejecting duct 80 by the air blown out of an air nozzle 92 to be ejected into either container 76 or 78 by the above mentioned determining action. In the embodiment in the non-operational state of the determining cylinder 90 or the damper 88, the damper 88 is always urged to open the defective article duct 84 and the inspected circular seal members 10 are all ejected toward the defective article container 78. Incidentally, in the selecting mechanisn, in addition to the actions mentioned above, it is possible that the non-defective articles are ejected into the non-defective article container, and that the inspecting means is stopped in operation with a warning rendered by a lamp, buzzer or the like, when a defective article is detected.

As described hereinabove, the present invention enables the full automatic inspection of the external defects of the circular seal member 10 and the repetition of the above mentioned inspection makes it possible to perform fast and accurate inspection of the external defects.

Description will hereunder be given successively and detailedly of the arrangement and action of the optical defects detecting means for each of the above mentioned surfaces of the circular seal member 10, that is, the conical surfaces 10a and 10b, the projected portion 10c and the upper surface 10d.

Figure 4:
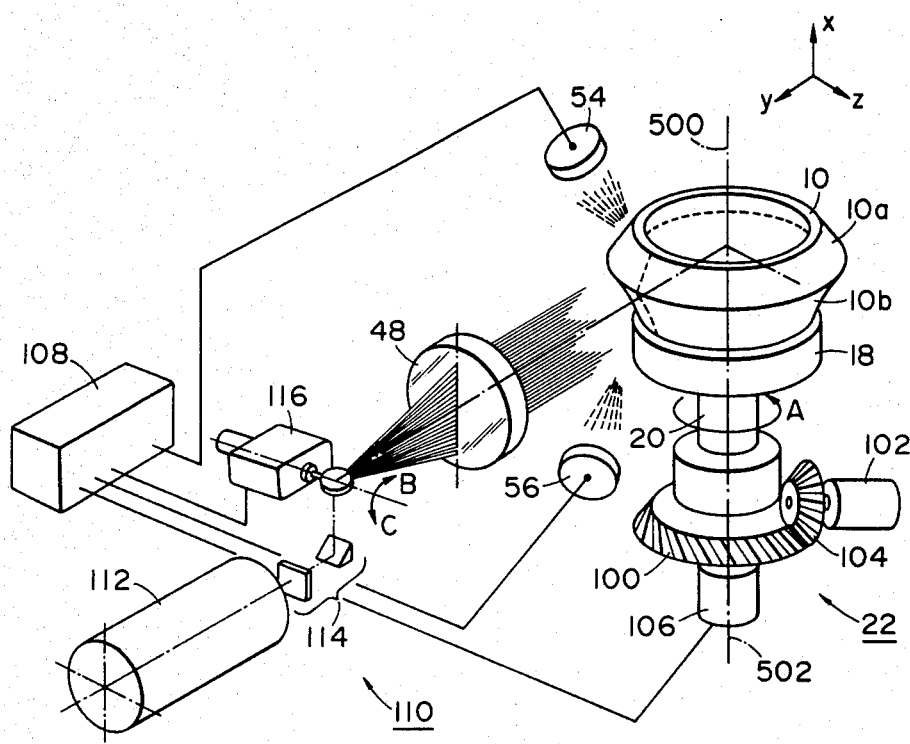
FIG. 4 is a schematic block diagram showing a preferred embodiment of a conical sealing surface inspecting mechanism in accordance with the teachings of the present invention.

Shown in FIG. 4 are essential portions of the conical sealing surface inspecting mechanism. The circular sealing member 10 is placed on the rotary stand 18 and the axis 500 of the circular seal member 10 is positioned by the above mentioned automatic delivery mechanism 24 substantially in alignment with the rotary axis 502 of the rotary stand 18. The rotary stand 18 is connected to the above mentioned rotary mechanism 22. More specifically, a bevel gear 100 is fixed to the rotary stand shaft 20 and is geared with a bevel pinion 104 which is fixed to a motor 102. Rotation of the motor 102 rotates the rotary stand 18 or the circular seal member 10 toward the direction indicated by an arrow A. Fixed to the lower end of the rotary stand shaft 20 is an encoder 106, which electrically detects the rotated position and angle of the circular seal member 10 as the rotated angle signals, and the defects detecting circuit 108 provided in the microcomputer 70 receives the signals.

Disposed immediately adjacent the circular seal member 10 is a polarizing scanning light source 110 provided in the optical system unit 46, and this polarizing scanning light source 110 includes laser 112. From the gaseous laser 112 such as helium neon laser, etc. monochromic and directional beams are are radiated and the beams sent into a light deflector 116 by way of a prism system 114. The light deflector 116 has a mirror which vibrates at its own vibrating cycle or which performs light deflecting action being synchronized with alternating current signals externally supplied, and adopted in the embodiment is a galvanomirror which can detect through wide angles. The deflecting axis of the light deflector 116 is provided perpendicularily to the rotary axis 502 of the rotary stand 18. Consequently, the deflected light reflected from the light deflector 116 advances toward the rotary axis 502, and further, this deflected light is controlled and scanned in accordance with the vibrations in the directions indicated by the arrows B and C of the light deflector 116. The scanning speed of the light deflector 116 by the above mentioned mirror vibrations is determined satisfactorily faster than the rotating speed of the rotary stand 18. The polarizing scanning light source 110 further includes the projecting lens 48, and the deflected light sectorially scanned is converted into parallel rays along the scanning surface by the projector lens 48. The parallel rays are scanned and irradiated to the conical surfaces 10a and 10b of the circular seal member 10. In other words, the rays scanned in parallel with one another by the projector lens can reject the change of the inspecting sensitivity derived from the variety and the decentering of the circular seal member 10. The rays, being in a condition of a flux, can remarkably increase the detecting and resolving power.

The above mentioned parallel rays from the polarizing scanning light source 110 are reflected by both of the conical sealing surfaces 10a and 10b of the circular seal member 10, and received by first photoelectric detectors 54 and 56 to be converted into electric signals. Both of the photoelectric detectors 54 and 56 are provided at the positions where the regularly reflected light can be received in such a state that the external defects cannot be detected on both of the conical sealing surfaces 10a and 10b and the detecting electric signals from both of the detectors 54 and 56 are supplied to the defect detecting circuit 108.

The inspection data from the rotary stand 18, the polarizing scanning light source 110 and the photoelectric detectors 54 and 56 are supplied to the above mentioned defect detecting circuit 108, and is processed at least per full rotation of the rotary stand 18. The irregular reflection caused from the defects on the conical sealing surfaces 10a and 10b detects the defects and the output from the defect detecting circuit 108 controls the operation of the indication section 74 and the selecting mechanism 75.

The inspecting mechanism of the conical sealing surfaces has such an arrangement as described hereinabove and its action will be described hereunder.

In the embodiment, a full rotation of the rotary stand 18 completes the inspection of one piece of circular seal member 10, and then, next seal member 10 is placed on the rotary stand 18 by the automatic delivery mechanism 24. At this time the axis 500 of the circular seal member 10 is placed to be substantially in alignment with the rotary axis 502 of the rotary stand 18. The misalignment between the axis 500 and the axis 502, however, does not affect the inspection ability in the present invention since the irradiating parallel rays from the polarizing scanning light source 110 has enough irradiating range covering the conical sealing surfaces 10a and 10b which require sufficient inspection, and the regularly reflected light from both of the conical sealing surfaces 10a and 10b are received by the photoelectric detectors 54 and 56 which have sufficiently large areas for the regularly reflected light even if the position is slightly shifted.

After the circular seal member 10 is placed on the rotary stand 18, the rotary stand 18 is driven and rotated at constand speed by the motor 102, and at the same time from the polarizing scanning light source 110 the scanning rays are irradiated to the conical sealing surfaces 10a and 10b at a faster scanning speed than the rotating speed of the rotary stand 18.

Figure 5:
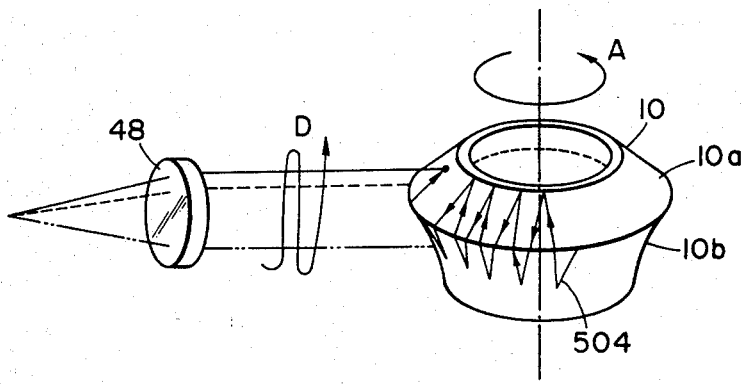
FIG. 5 is an explanatory view showing polarizing scanning state of the conical sealing surface in FIG. 4.

FIG. 5 shown such a state that the conical sealing surfaces 10a and 10b of the circular seal member 10 are scanned all over by the rays irradiated through the projecting lens 48. The rotation of the circular seal member 10 in the direction indicated by the arrow A and the reciprocating scanning movement D of the irradiated rays provides light dot locus shown as 504, and over the entire conical sealing surfaces 10a and 10b can be scanned during a full rotation of the rotary stand 18. Incidentally, the light dot locus is roughly illustrated in order to simplify the description, but the light dot locus 504 actually becomes extremely dense since the deflecting speed of the polarizing scanning source 110 is determined to be large as compared with rotating speed of the rotary stand 18.

The irradiated rays through the projector lens 48 are reflected from both of the conical sealing surfaces 10a and 10b and advance forward to the photoelectric detectors 54 and 56 as regularly reflected light. In case there exist some defects on both of the conical sealing surfaces 10a and 10b, the light is irregularly reflected, and it is understood that the value of the detected signals from the photoelectric detectors 54 and 56 is remarkably decreased when the defective portion is scanned. Accordingly, detection of this fluctuated signal output by the defect detecting circuit 108 can inspect the quality of the circular seal member 10.

Figure 6:
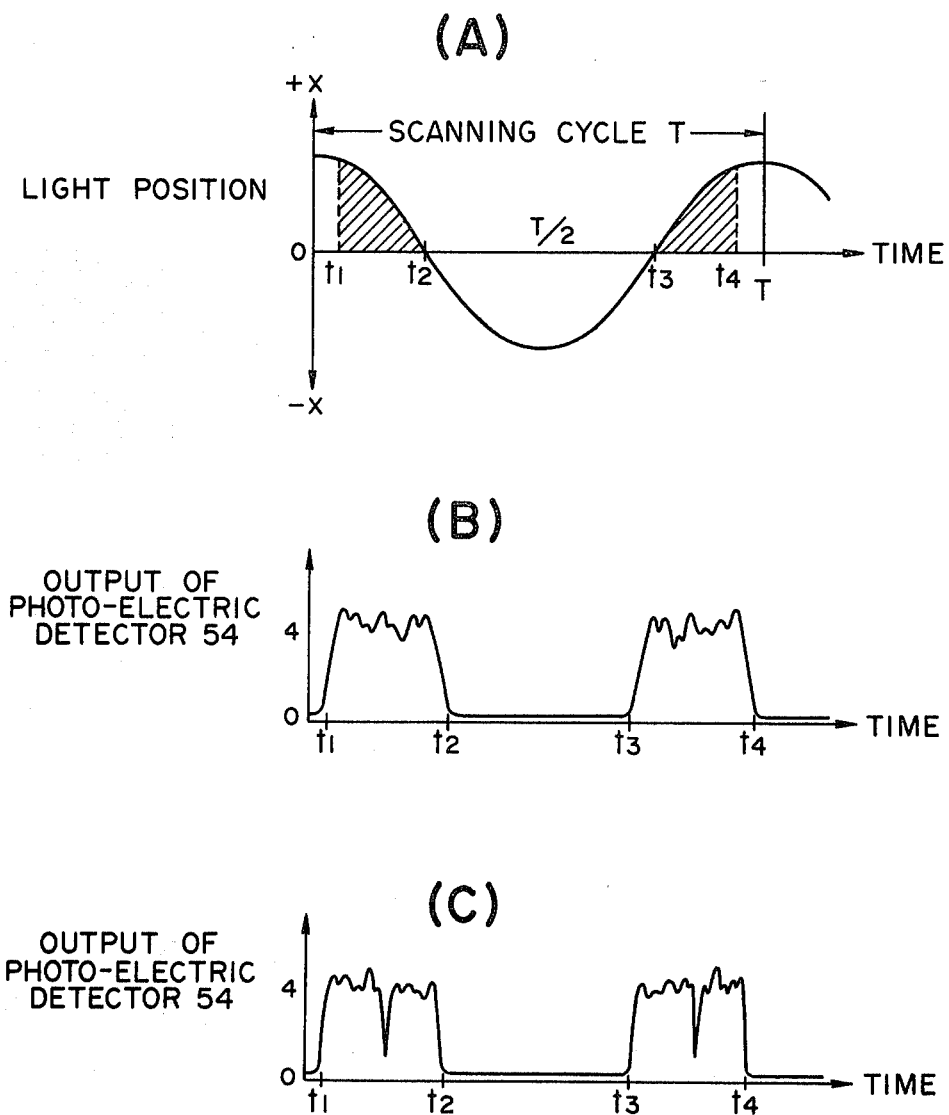
FIGS. 6A, 6B, 6C are wave form charts showing photoelectric converting action in FIG. 4.

FIG. 6 shows wave form charts of the photoelectric detector 54 in the one scanning cycle of the irradiated rays. As evident from FIG. 6 (A), polarizing scanning start from upper part of the conical sealing surface 10a and complete its scanning of the conical sealing surface 10a between the time $t_1$ and $t_2$. The scanning of the conical sealing surface 10b is performed by downward scanning and reaches the lowest scanned point at the time of T/2, where the scanning is inverted to start upward scanning over the conical sealing surface 10a between the times $t_3$ and $t_4$ after scanning the conical sealing surface 10b, and one scanning action completes at the time T.

FIGS. 6 (B) and (C) show electric output signals of the photoelectric detector 54. (B) shows normal surface state of the conical sealing surface 10a and (C) shows that there is a defect on the conical sealing surface 10a. As evident from FIG. 6 (B), at the time $t_1$–$t_2$ and $t_3$–$t_4$, approximately constant detective signals are obtained from the photoelectric detector 54 although there are some fluctuations and it is possible to determine that there is no defective part in this scanned region since the regularly reflected light proves to be stable. On the other hand, in FIG. 6 (C), there are parts where the electric output signals show remarkably low as a result of irregular reflection by external defects and it is possible to determine that the conical seal member 10a has external defects of flaw.

Figure 7:
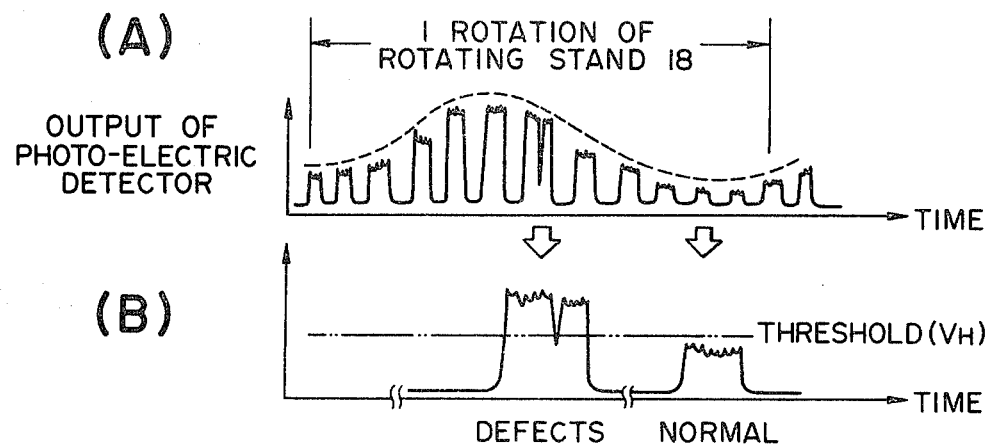
FIGS. 7A, 7B and 8A, 8B are wave form charts showing problems of conventional photoelectric converting action.

As mentioned above, the continuous process of the electric detecting signals from the photoelectric detector 54 or 56 during a full rotation of the rotary stand 18 can detect the external defects all over the conical sealing surfaces 10a and 10b, but there may be a case that the signals fluctuate without any external defect during a full rotation of the rotary stand 18 due to nonuniformity of reflecting factor depending upon the part of the conical sealing surfaces 10a and 10b and misalignment between the circular seal member 10 and the rotary stand 18, etc. FIG. 7 (A) shows such a case that periodical fluctuation arises during a full rotation of the rotary stand 18 due to various causes mentioned above, and it is impossible to obtain correct result of inspection by general comparison with signals including large fluctuations from the defect detecting circuit. FIG. 7 (B) shows such a state that a fixed threshold value VH is applied to the above mentioned detecting signals during a full rotation of the rotary stand. In case the fixed threshold value VH is determined to be large to some extent in order to prevent noises from mixing thereinto, there arises such case that the normal signals are determined to be defective as shown in FIG. 7 (B), and it is difficult to use such fixed threshold value comparison type defect detecting circuit.

Figure 8:
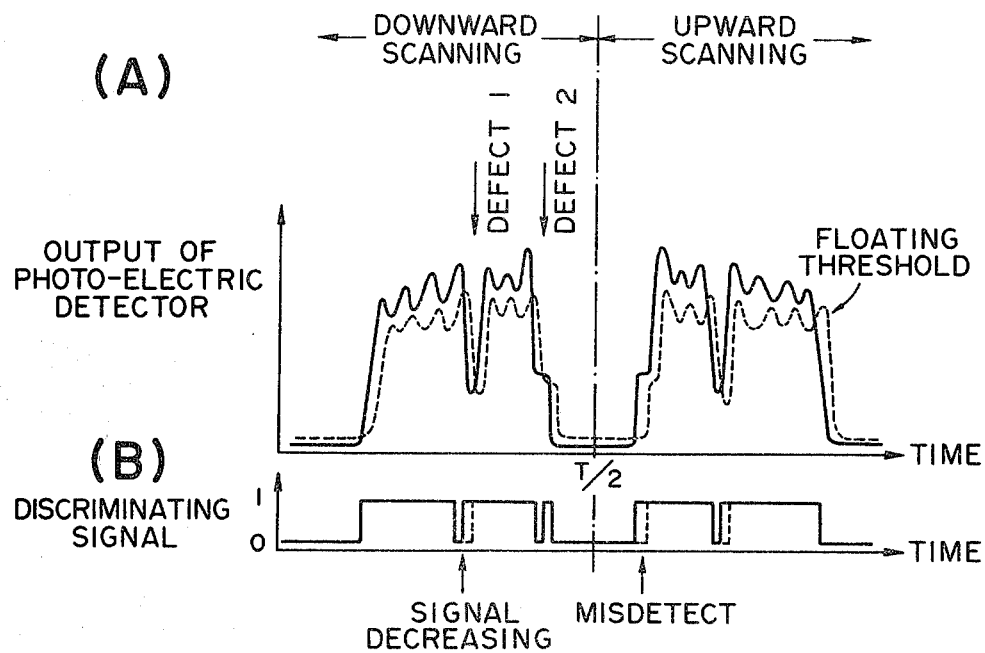

In order to obviate the above mentioned disadvantage, a circuit for the floating threshold value system has been proposed as in the other conventional defects detecting system. As shown in FIG. 8 (A), such a circuit arrangement has been adopted that the floating threshold value indicated by a dotted line is provided having a little delay behind the detected signal value indicated by a solid line, and as a result of comparison between the detected signal value and the floating threshold value, a discriminating signal as shown in FIG. 8 (B) is emitted. Such floating threshold value system can eliminate the influence of periodical detected signal value fluctuations, etc., but the time delay of floating threshold value detects the actual defect in reduced scale, and the defects at the starting point of the scanning and the completing point of the scanning at the conical sealing surface 10a cannot be detected, and so on.

Figure 9:
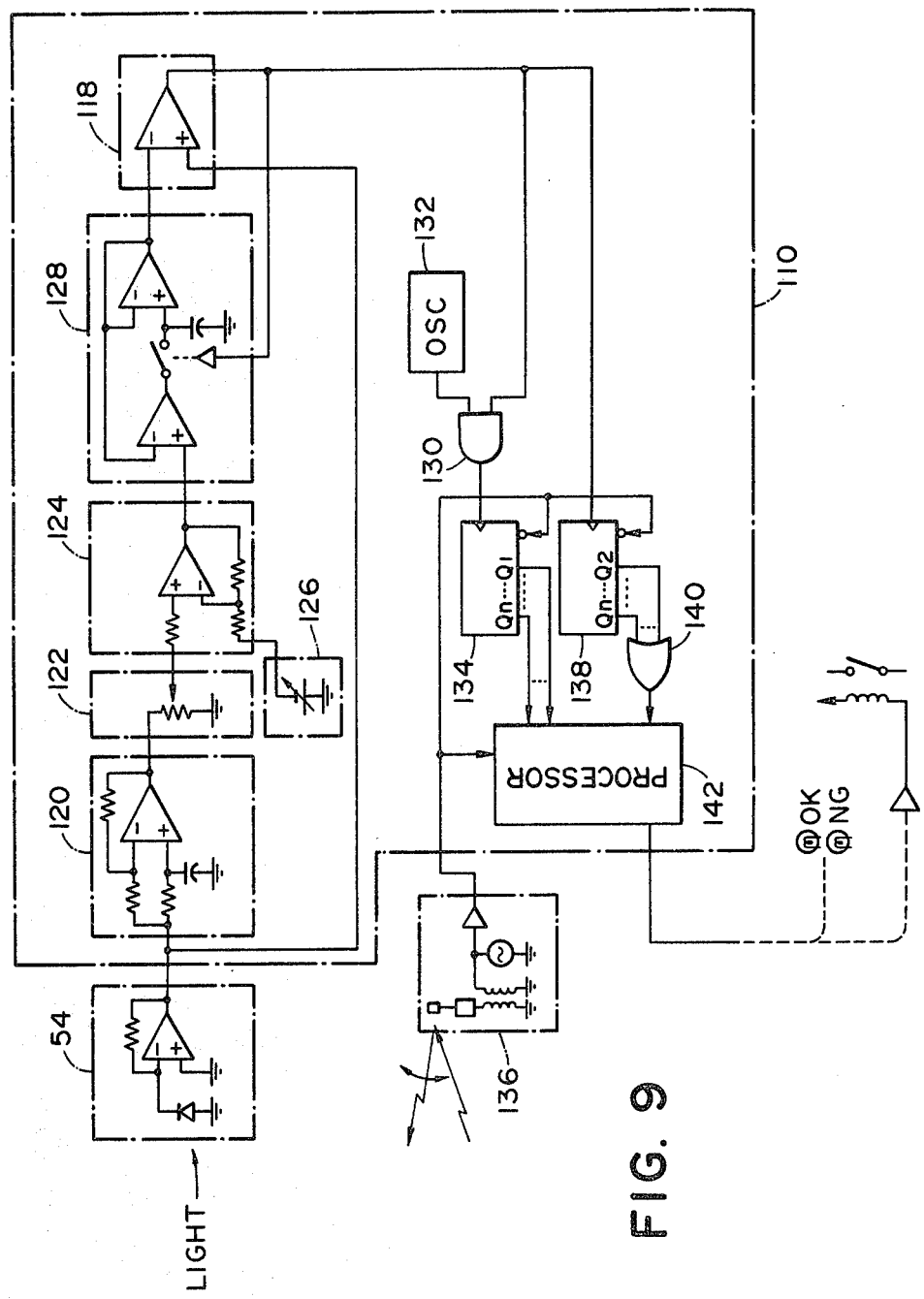
FIG. 9 is a circuit diagram showing a specific example of a defect detecting circuit being used with the embodiment in FIG. 4.

In order to correct the drawbacks mentioned above, in the embodiment of the present invention, the defect detecting circuit 110 shown in FIG. 9 is adopted and offered therein is the circuit which the floating threshold value system is further improved and the external defects can be reliably detected.

FIG. 9 shows a processing circuit on the side of photoelectric detector 54 and the side of photoelectric detector 56 also has the same processing circuit. The photoelectric detector 54 includes photo-diodes, etc. and converts the regularly reflected light from the conical sealing surface 10a into the electric signals having the quantity of electricity corresponding to the quantity of received reflected light. One output of the photoelectric detector 54 is supplied to the positive input terminal of a comparator 118, and the other output is supplied to the negative input of the comparator 118 after being converted into the floating threshold value. In other words, the output of the photoelectric detector 54 is delayed in a delay circuit 120 for a certain period of time and is attenuated in an attenuator 122. Consequently, the output from the attenuator 122 decrease the fluctuations of the regularly reflected light from the normal surface and, on the other hand, can provide sufficiently detectable signal characteristic to the irregularly reflected light from the defective surface. To the output of the attenuator 122 a bias voltage of a bias voltage generator 126 is added in an adder 124. This bias voltage is provided at a little larger voltage value than a dark voltage of the photoelectric detector 54 and, as a result, the floating threshold value is fed from the adder 124. In the embodiment, it is characterized that the floating threshold value of the adder 124 is supplied to the above mentioned comparator 118 by way of a sample hold circuit 128. Fed to the hold input of the sample hold circuit 128 is an output of the comparator 118 and the floating threshold value output from the sample hold circuit 128 is held at the threshold value when the defect detecting signal is fed from the comparator 118. When the detecting signal from the comparator 118 goes off, the holding action of the sample hold circuit 128 is released and the floating threshold value from the adder 124 is fed to the comparator 118 as it is.

As mentioned hereinabove, the defect detection is performed on the side of the photoelectric detector 54, and the output of the comparator 118 is further electrically processed to be converted into signals which determine whether the circular seal member is non-defective or defective. The above mentioned defect detecting signal generating action will hereunder be described with reference to the wave form charts of FIG. 10.

Figure 10:
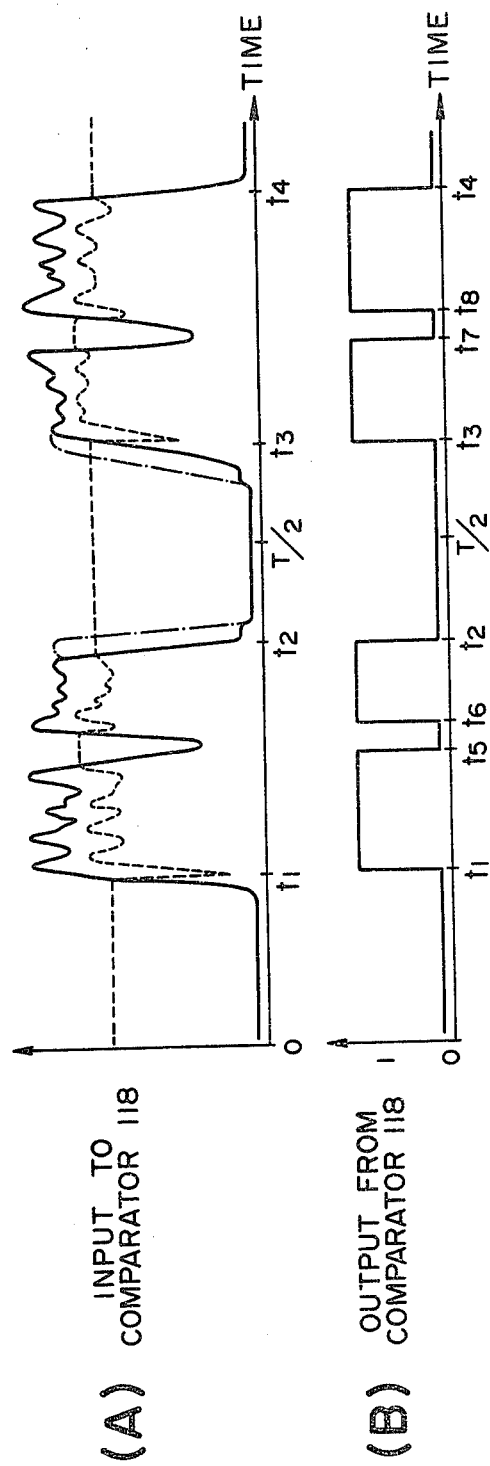
FIGS. 10A, 10B are wave form charts showing defect detecting action in FIG. 9.

FIG. 10 (A) shows two inputs of the comparator 118. A solid line designates the positive input directly supplied from the photoelectric detector 54, and a broken line denotes the floating threshold value input supplied from the sample hold circuit 128. FIG. 10 (B) shows the output of the comparator 118. In the normal state of the conical sealing surface 10a, the signal "1" is emitted, but in the defective state the signal "0" is emitted.

In the initial state until the time of $t_1$ when the surface state of the conical sealing surface 10a is detected, the regularly reflecting light is not supplied to the photoelectric detector 54 and the output of the comparator becomes "0". At this time, the sample hold circuit 128 is brought into a hold mode and holds the previous floating threshold value. At the time of $t_1$, light scanning to the conical sealing surface is started, and the output of the photoelectric detector 54 goes up when the regularly reflected light is received. When the output of the photoelectric detector 54 goes up higher than the threshold value held in the sample hold circuit 128, the comparator 118 is inverted to emit the signal "1". Consequently, the holding state at the sample hold circuit 128 is released, and the floating threshold value of its output delays the output voltage of the photoelectric detector 54 to emit further attenuated voltage. In case there is a defect on the surface the quantity of light received by the photoelectric detector 54 suddenly decreases when the scanned rays reach the defective point, and, as a result, the detecting output is also decreased suddenly. At the time of $t_5$, the output of the comparator 118 becomes "0" to emit the defect detecting signals, and hold the sample hold circuit 128 at this moment to be able to hold the floating threshold value voltage at this time. When the scanned rays pass the defective point and the quantity of light received returns to the normal state, the output of the photoelectric detector 54 goes up higher than the output of the sample hold circuit 128 and the comparator 118 is inverted at the time of $t_6$ to have the sample hold circuit 128 return to the tracing mode. Accordingly, during the period of $t_5$-$t_6$ when the defective point is scanned, the sample hold circuit 128 holds its output value to reliably prevent the decrease of the defect detecting signals and non-detection on the opposite ends of the scanning region. At the time of $t_3$-$t_4$ when the scanning action is performed upward over the conical sealing surface 10a, the same sample hold action of the sample hold circuit 128 is performed at the time of $t_7$-$t_8$ as described above.

As described hereinabove, according to this embodiment, the drawbacks of the conventional floating threshold value system are obviated and the comparative threshold value can be adequately adjusted by following the change in quantity of light reflected so that the conventional defect reduction and inability of discrimination at the projected portion can be obviated.

In FIG. 9, the defect detecting signal of the comparator 118 is supplied to one input terminal of gate 130 in order to perform digital process, and is taken AND with clock pulse of a clock oscillator 132 which is supplied to the other input terminal of the gate 130. The clock pulse passing through the gate 130 with half cycle of deflecting scanning is counted at a first counter 134. The counted value of the first counter 134 is reset at every half cycle of the deflecting scanning by the polarizing control circuit 136 of the light deflector 116, and the counted value of the first counter 134 decreases with the increase of the defect detecting time within the half cycle of the scanning cycle. Accordingly, the size of the defect can be detected as digital value.

At the same time, the output of the comparator 118 is directly counted in a second counter 138. The second counter 138 is also reset at every half cycle of the deflecting scanning by the output of the deflecting control circuit. The outputs of both counters 134 and 138 are supplied to a processor 142 directly or by way of OR gate 140 and the counted value from both counters 134 and 138 per full rotation of the rotary stand 18 is operated and processed. Accordingly, in the processor 142, the counted value of the first counter 134 detected at every half cycle is compared with the previous counted value, and occurrence of a sizable difference between the two counted values makes it possible to detect the external defects. For elongate defects at right angle to the polarizing scanning direction, the second counter 138 can make defect discrimination through its counted value. The fluctuation in the counted value in the first counter 134 makes it possible to detect an elongate defect in the polarizing scanning direction as the fluctuation in counted values. On the defects at right angle to the polarizing scanning direction the difference between two counted values in the first counter 134 becomes smaller, but the defects can be detected out of the second counter 138 at every half cycle. The operator 142 can emit a defect signal when the above mentioned situation continues during the predetermined period. The second counter 138 emits counting values exceeding 2 in case there is one defect at least at every half cycle. In order to do this, OR gate 140 operates OR operation of Q output exceeding 2 bit from the second counter 138, and emits defect detecting signal from OR gate 140 to the processor 142 when there is one piece of defects at least. The processor 142 operates toward the rotating direction of the rotary stand 18 to discriminate the defects.

As described hereinabove, the non-defective-defective article discrimination signals of the article defect detecting circuit 110 effects non-defective-defective discrimination of the circular seal member 10 in the indication section 74, and the selecting mechanism 75 can reject the defective circular seal members.

An inspecting mechanism for the projected portion 10c in FIGS. 2 and 3 will hereunder be described with reference to FIGS. 11 and 12.

Figure 11:
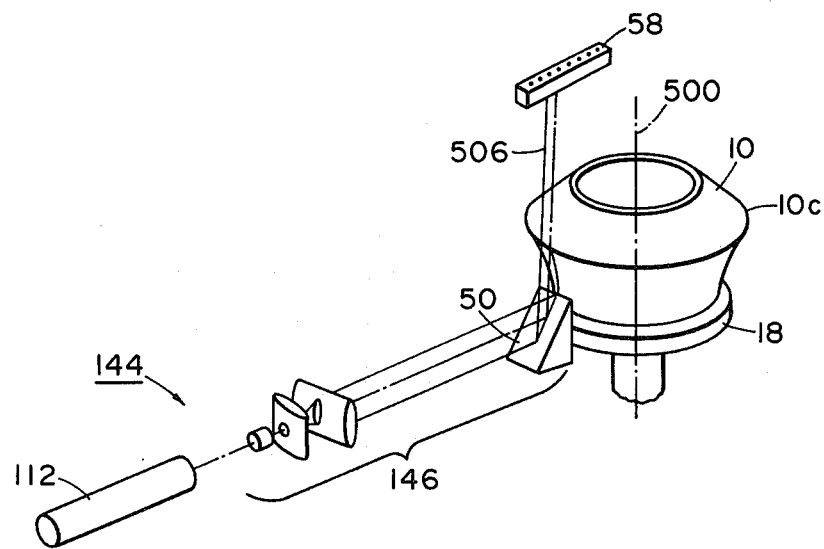
FIG. 11 is a schematic block diagram showing a preferred embodiment of the projected portion inspecting mechanism in accordance with teachings of the present invention.
Figure 12:
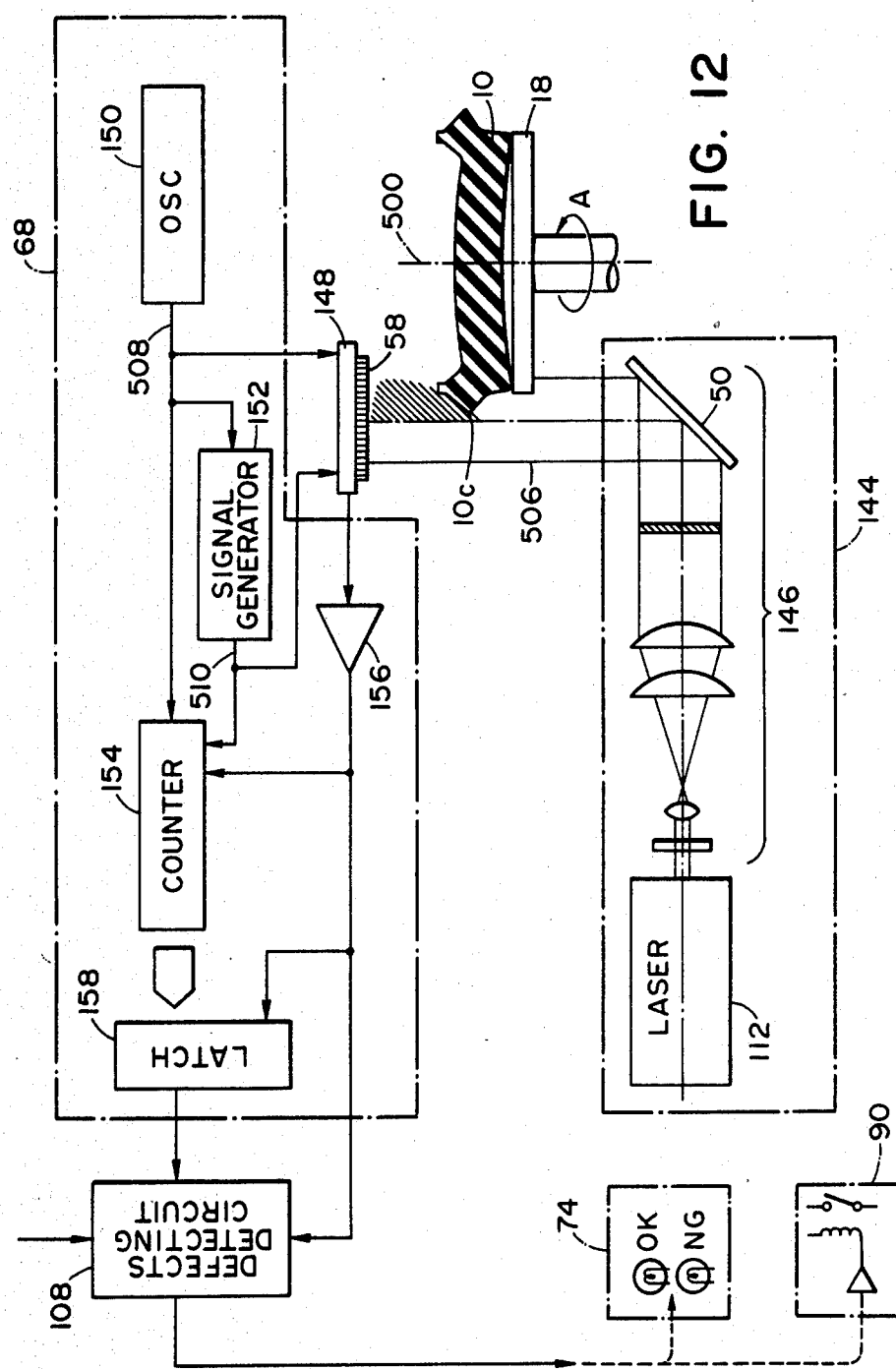
FIG. 12 is a general explanatory view showing the circuit arrangement in FIG. 11.

In FIGS. 11 and 12, in the optical system unit 46 is provided therein with a slit light flux generating device 144. The slit light flux generating device includes a parallel light flux generating light source consisting of lamp, laser, etc. A laser 112 is used in this embodiment and a lens and mirror system 146 which converts the parallel light flux into a slit light flux illustrated in hatching (FIG. 12) in order to irradiate externally. The slit light flux 506 reflected from a projector mirror 50 is irradiated to the projected portion 10c of the circular seal member 10. On the light path of above mentioned slit light flux 506 the photoelectric detecting array 58 is provided along the slit light flux 506, that is, along the radial direction of the rotary stand 18 so that the slit light flux not interrupted by the projected portion 10c of the circular seal member 10 can be photoelectrically converted. In the embodiment, the photoelectric detecting array 58 consists of a diode array, etc. arranged in one line to form a self scanning type photoelectric detecting array together with the scanning circuit 148 to which the diode array is electrically connected. A projection detecting circuit 68 is provided in order to detect the projection of the projected portion 10c in response to an output of the photoelectric detecting array 58 and a clock oscillator 150 is provided in the projection detecting circuit 68 in order to scan and drive the photoelectric detecting array 58. A scanning clock 508 of the clock oscillator 150 drives the scanning circuit 148 successively, and the photoelectric detecting array 58 is photoelectrically converted from the left side of FIG. 12 one after another. In order to trigger to start scanning of the scanning circuit 148, an output of the clock oscillator 150 is supplied to a scanning start signal generator 152 and the scanning start signal 510 starts scanning in the scanning circuit 148. The scanning start signal 510 is further used as a reset signal of a counter 154 counting the above mentioned scanning clock and the counter 154 starts counting the scanning clock from "0" upon starting scanning of the photoelectric array 58. A photoelectrically converting signal of the photoelectric detecting array 58 is supplied to a comparator 156, and the comparator 156 consists of one shot circuit in the embodiment. In case ray irradiation is performed to the scanned element of the photoelectric detecting array 58, no output is emitted from the comparator 156, but an output is supplied from the comparator 156 when the scanned element of the photoelectric detecting array 58 moves into a shadow of the projected portion 10c and does not receive ray irradiation, and the projection of the projected portion can be detected. More specifically, the output of comparator 156 is supplied to a count stop input terminal of the counter 154 and the counter 154 stops counting the scanning clock 508. The counted value of the counter 154 is latched in a latch circuit 158 and a latch value of the latch circuit 158 is supplied to the defect detecting circuit 108 as a detecting signal of the projection detecting circuit 68 at every one scanning action of the photoelectric detecting array 58. Additionally, an output of the comparator 156 is supplied to the latch circuit 158 as a load signal and to the defect detecting circuit 108 as an interrupt signal.

In the embodiment, the projected portion defect detecting mechanism has such an arrangement as described above, and the action of this mechanism will hereunder be described.

When the circular seal member 10 to be inspected is delivered from the automatic delivery mechanism 24 to the rotary stand 18, the rotary stand 18 is rotated and, at the same time, the slit light flux 506 is irradiated in the direction of the axis of the circular member, i.e. from the lower part of the drawing upward to the projected portion 10c of the circular seal member 10 from the slit light flux generating device 144. This slit light flux 506 is of an elongate shape in the radial direction of the rotary stand 18 in cross section, and the width in the longitudinal direction is determined to sufficiently cover the diameter of the circular seal member 10, that is, the projected portion 10c, even if some changes are made, and different and various kind of the circular seal member 10 can be inspected by the same detecting means.

Irradiation of slit light flux 506 accurately projects the projection of the projected portion 10c on the photoelectric detecting array 58. More specifically, in the area where the slit light flux 506 is not shielded by the projected portion 10c, the slit light flux reaches the photoelectric detecting array 58 as it is and the projection becomes "bright". On the other hand, the shadow portion shielded by the projected portion 10c becomes "dark". A border between the above mentioned "dark" and "bright" portions accurately indicates the projection of the projected portion 10c. Accordingly, in the optical inspection of the present invention, it is not required to bring the projected portion 10c in focus and the projected portion 10c can be placed at an optical position within the slit light flux 506. When the diameter or the like of the circular seal member 10 is changed, no adjustment is required and the extremely practical inspecting means can be obtained.

The black and dark border of the photoelectric detecting array 58 is detected by the projection detecting circuit 68 and a border signal is discriminated on which element of the photoelectric detecting array 58 has such border. This discriminating action is performed by well-known means. For example, each of the elements of the photoelectric detecting array 58 is assigned with an address and each address can be discriminated by the counted value of the scanning clock 508. In other words, the self scanning type photoelectric detecting array scans each of the element one after another in accordance with the scanning clock 508 in response to the scanning start signal 510 and feeds the quantity of light received by each of the elements as a signal of the system when the scanning clock 508 is synchronized therewith. This photoelectrically converting signal becomes "0" immediately after the scanning of the bright and dark border corresponding to the projected portion 10c and the counted value in the scanning clock at this time is counted in the counter 154 to be held in the latch circuit 158. This held value corresponds to the specific address of the photoelectric detecting element of the bright and dark border and is fed from the projection detecting circuit 68 to the defect detecting circuit 108 as the projection detecting signal.

In the present invention, the rotating speed of the rotary stand 18 is determined at a sufficiently slow speed compared with one scanning cycle of the photoelectric detecting array 58, and the projected portion 10c is completely inspected in its projection.

The defect detecting circuit 108 compares the projection detecting signal per full rotation of the rotary stand 18, and the defects can be detected on the basis of a sudden signal value fluctuation at a projection point having the external defects. This defect detection is compared at every scanning of the photoelectric detecting array 58 in order to reject the periodical fluctuation caused by a non-coaxial state between the axis of the circular seal member 10 and the axis of the rotary stand 18 and the like, and sudden fluctuation of the signal value at the time of defect detection shows the above mentioned defect detection. The output of the defect detecting circuit 108 operates the indication section 74 and the selecting mechanism 75 to perform non-defective article indication to reject the defective articles.

An inspecting mechanism for the external surface 10d illustrated in FIGS. 2 and 3 will hereunder be described with reference to FIG. 13.

Figure 13:
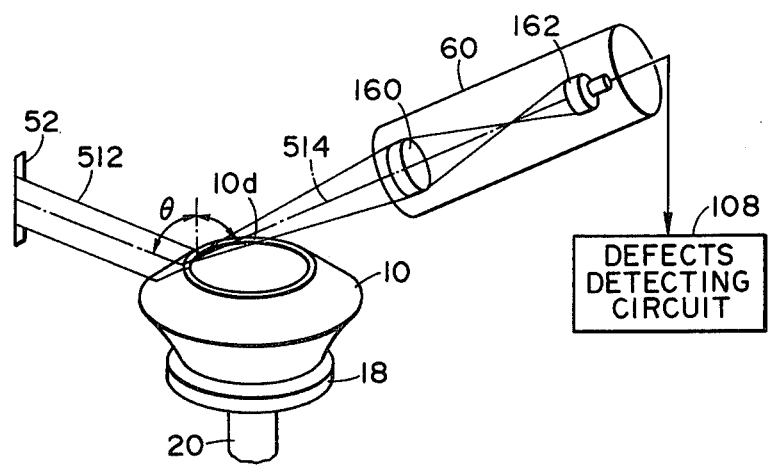
FIG. 13 is a schematic block diagram showing a preferred embodiment of the upper surface inspecting mechanism in accordance with the teachings of the present invention.

The slit light flux divided from the above mentioned slit light flux generating device 144 is irradiated at a large incidence angle $\theta$ to the external surface 10d of FIG. 13 as slit light flux 512 traversing the external surface 10d by way of slit section 52 shown in FIGS. 2 and 3.

The reflected light 514 reflected at the upper surface 10d of the circular seal member 10 is converted into electric signal at the second photoelectric detector 60. The photoelectric detector 60 in the embodiment includes a condenser 160 and a photoelectric converter 162. The regularly reflected light from the external surface 10d is received and converted into electric signal corresponding to the received quantity of light, and this electric signal is supplied to the above mentioned defect detecting circuit 108.

The output of the defect detecting circuit 108 is supplied to the indication section 74 and the selecting mechanism 75 so that non-defective-defective article discrimination of the external surface 10d of each circular seal member 10 can be indicated and the defective circular seal member 10 can be rejected.

The planar surface inspecting mechanism has such an arrangement as described hereinabove and the action of this mechanism will hereunder be described.

The slit light flux 512 irradiated toward the planer surface 10d is directed toward the radial direction of the circular seal member 10 in its longitudinal direction. Consequently, the slit light flux 512 is always irradiated to the planer surface 10d without any influence such as change in dimensions and varieties, misalignment with the axis of the rotary stand 18, the strains of the circular seal member 10, etc. The incidence angle θ of the slit light flux 512 is determined to be large, approximately 70 degrees in the embodiment, and as a result, the strong reflected light 514 can be produced in the regularly reflected direction against the circular seal member 10 made from the material of low reflectance such as black rubber so that effective reflecting action can be obtained with a little noise mixed therein. A large incidence angle θ makes it possible to reliably contain the planar surface 10d within the area of the slit light flux 512 even if the width of the planer surface 10d is considerably changed, and can offer such an advantage that the various types and kinds of the circular seal member 10 can be inspected by use of one and the same inspecting means.

As described hereinabove, during at least per full rotation of the rotary stand 18, the planer surface 10d can be irradiated all over by the slit light flux 512, and detection of the reflected light 514 at this time by the photoelectric detector 60 can inspect over the entire planer surface 10d. In other words, when the planer surface 10d is normal, the reflected light 514 can be received with approximately uniform quantity of light, and the electric signal of the photoelectric detector 60 becomes approximately constant in value. In case there is external defects on the planar surface 10d, the reflected light 514 is considerably decreased due to irregular reflection and the electric signal of the photoelectric detector 60 is also decreased to a considerable extent. The electric process of the fluctuation of this electric signal value by the defect detecting circuit 108 makes it possible to detect the defect reliably and with high precision.

The condenser 160 of the above mentioned photoelectric detector 60 limits the visual field and the visual direction of the optical detection and effectively prevents the incidence of background light and diffused light to eliminate noises mixing thereinto. The optical axis is determined approximately to the regularly reflected direction, but it is unnecessary to bring the external surface 10d in focus. The visual field and the visual direction are also determined to have sufficiently wide region so that the better optical detecting action can be accomplished even if the position of the planer surface 10d is slightly moved and the size and the placed location on the rotary stand 18 are changed.

Figure 14:
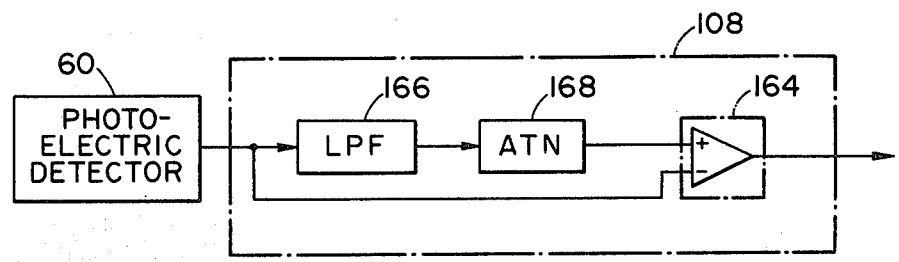
FIG. 14 is a circuit diagram showing a preferred embodiment of a defect detecting circuit in FIG. 13.

As mentioned above, the output of the photoelectric detector 60 represents the change corresponding to the external defects, which non-defectiveness or defectiveness of the circular seal member 10 can be discriminated, and preferred embodiment of the defect detecting circuit 108 processing electric signals illustrated in FIG. 14.

The reflected light 514 from the planer surface 10d has the periodical fluctuation per full rotation of the rotary stand 18, and this fluctuation causes in the angle of the planer surface, non-coaxial state of the circular seal member 10 or the like despite there is a defect or not. In order to eliminate this periodical fluctuation, the defect detecting circuit 108 has such a function that the external defect can be discriminated by comparison of the floating threshold value corresponding to the detecting signal with the detecting signal. In FIG. 14, the defect detecting circuit 108 includes a comparator 164. To the negative input terminal, the detecting signal is directly supplied and to the positive input terminal, the floating threshold value corresponding to the detecting signal of the photoelectric detector 60 is supplied. In other words, the output of the photoelectric detector 60 goes through a low pass filter 166 and an attenuator 168 to eliminate high constituents therefrom as well as to perform predetermined attenuating action, and is supplied to the comparator 164.

Figure 15:
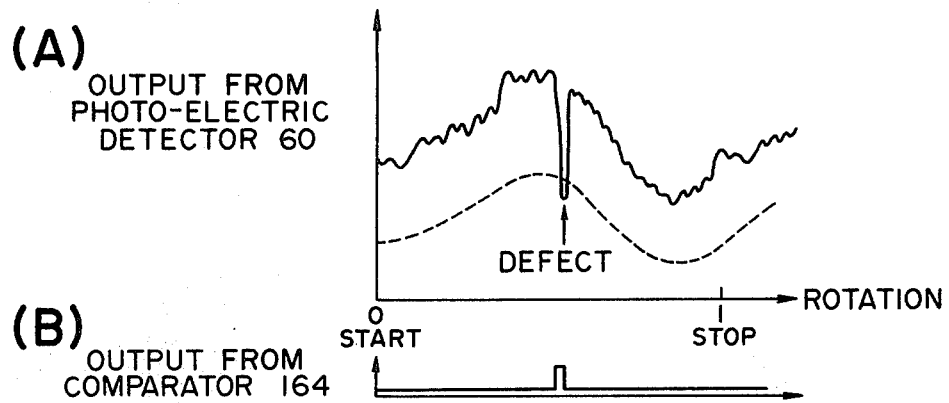
FIGS. 15A, 15B are wave form charts in explanation of the action in FIG. 14.

FIG. 15 shows a characteristics curve diagram of the defect detecting circuit 60. FIG. 15 (A) shows the output of the photoelectric detector 60 indicated by a solid line, and the floating threshold value indicated by a broken line which approximately traces this output, is eliminated high constituent therefrom and attenuated in voltage value. According to this floating threshold value system, such influence as ununiformity of reflectance spread over the planer surface 10d, non-coaxial state of rotation, change of the light source in the quantity of light, etc. is reduced, and uniform defect detecting accuracy can be always obtained. In FIG. 15 (A), the defective portion is shown as a portion decreased in its output to a considerable extent. Since the floating threshold value smooths sudden fluctuation through the action of the low pass filter 166, the output of the photoelectric detector 60 is lowered to less than the floating threshold value in the defective portion, and the defect signal "1" can be obtained from the comparator 164 as shown in FIG. 15 (B).

Incidentally, in the embodiment described above, the circular member is described as the circular seal member, but the present invention can be applied to such circular member as a rubber plug, a rubber ring or the like.

As described hereinabove, according to the present invention, the minute external defects which have not been detected by eye sight can be detected with extremely high accuracy. A large number of circular seal members can also be inspected automatically and rapidly without touching the circular seal member to be inspected, and the defectiveness and the low durability of a circular seal member caused by a defect on the external surface can be reliably prevented.

According to the present invention, the automatic inspecting means can be arranged immediately after the detaching process so that the damages to the cutting blade can be rapidly found through the defect of the external surface to remarkably lower the rejection rate of the circular seal members.

Furthermore, according to the present invention, the effective inspecting means can be offered for automobile brake cups, etc., and the accurate inspection can be performed without applying any mechanical stress thereto and without touching the circular seal member made from soft material such as rubber, etc.

What is claimed is:

1. Apparatus for detecting an external defect of a circular member comprising:
   a rotary stand rotatably mounted on a detecting table and placed thereon with the circular member to be rotated;
   an automatic delivery mechanism for delivering circular members to be inspected one after another to said rotary stand in a predetermined posture;
   a scanning light source for irradiating the detecting rays, which are controlled and scanned at a speed faster than the rotating speed of said rotary stand substantially in parallel with a rotary axis of said rotary stand, to a conical surface of the circular member, said scanning light source comprising:
a laser radiating a directional beam;
a light deflector having a deflecting axis provided perpendicularly to the rotary axis of the rotary stand, and polarizing and scanning said laser; and
a projector lens projecting the deflected light sectorially scanned to conical surfaces as parallel rays; and
a photoelectric detector for receiving the regularly reflected light from the conical surface to convert same into electric signals;
a defect detecting circuit for continuously processing said electric signals of said photoelectric detector at least per full rotation of said rotary stand and detecting a surface defect of said circular member, said defect detecting circuit comprising:
a delay circuit delaying output of the photoelectric detectors for a certain period of time;
an attenuator attenuating an output of said delay circuit;
an adder adding a bias voltage to an output of said attenuator and feeding a floating threshold value;
a sample hold circuit sample holding and feeding the floating threshold value; and
a comparator comparing the output from said sample hold circuit with the output from the photoelectric detector to feed a defect detecting signal as well as holding the floating threshold value of said sample hold circuit by the defect detecting signal;
whereby said threshold value is adjusted to the most suitable value in accordance with the fluctuation of the reflected light; and
a selecting mechanism for selecting non-deflecting circular members from the defective ones upon completion of inspection in response to the defect detecting signals of said defect detecting circuit;
so that the surface defects can be optically inspected without touching the circular members.

2. Apparatus according to claim 1, wherein said defect detecting circuit further comprises:
a gate having two input terminals, one input terminal thereof being connected to said comparator for receiving said defect detecting signals;
a clock oscillator connected to the other input terminal of said gate for generating clock pulses, said clock pulses being passed through said gate in the absence of said defect detecting signals from said comparator;
a first counter connected to said gate for counting said clock pulses during a half cycle of said scanning; and
a processor connected to said first counter for processing the value counted by said first counter;
thereby detecting the size of a surface defect of said circular member.

3. Apparatus according to claim 2, wherein said defect detecting circuit further comprises a second counter connected to said comparator, for counting said defect detecting signals from said comparator during the half cycle of said scanning to thereby detect the number of surface defects of said circular member.

4. Apparatus according to claim 1, further comprising:
a slit light flux generating device for irradiating the slit light flux at an incidence angle large enough to cause specular reflection to an upper surface of said circular member;
a second photoelectric detector for receiving the specularly reflected light from the upper surface to convert the specularly reflected light into electric signals; and
a second defect detecting circuit for continuously processing said electric signals of said second photoelectric detector at least per full rotation of said rotary stand;
thereby detecting defects on the conical and upper surfaces of said circular member.

5. Apparatus according to claim 4, wherein said slit light flux generating device comprises:
a laser device;
a lens and mirror system converting a laser beam from said laser device into a slit light flux;
a slit section for directing the slit light flux to the upper surface of the circular member; and
said photoelectric detector comprises:
a condensor for receiving reflected rays from the upper surface of the circular member; and
a photoelectric convertor for converting the received rays through said condensor into electric signals.

6. Apparatus according to claim 1, further comprising:
a slit light flux generating device for irradiating a slit light flux to a radially outwardly projecting portion of the circular member in direction of the axis thereof;
a photoelectric detecting array for receiving rays not interrupted by the projected portion to convert same into electric signals;
a projection detecting circuit for detecting a projection in accordance with said received rays in response to the output of the photoelectric detecting array; and
a third defect detecting circuit for continually processing the electric signals of the projection detecting circuit at least per full rotation of the rotary stand;
thereby detecting defects on the conical and projected surfaces of said circular member.

7. Apparatus according to claim 6, wherein said slit light flux generating device comprises:
a laser device for generating a laser beam of light;
a lens and mirror system for converting said laser beam of light into a slit light flux; and
a projector mirror for irradiating a slit light flux to the projected portion of the circular member; and
said photoelectric detecting array forms a self-standing type photoelectric detecting array and comprises:
a diode array arranged and provided in one line along the radial direction of the rotary stand; and
a scanning circuit connected to said diode array.

8. A method of detecting an external defect of a circular member comprising:
delivering circular members one after the other to a detecting section in a predetermined posture, said circular members being rotated at said detecting section;
irradiating a detecting ray for scanning to a conical surface of said circular member;

receiving a specularly reflected light from the conical surface of the circular member for converting the specularly reflected light into an electric signal;

delaying said electric signal for a certain period of time;

attenuating said delayed signals;

adding a biased voltage to said attenuated signal and feeding a floating threshold value;

transmitting a signal representative of said floating threshold value through a sampling and holding means;

comparing said transmitted signal with said electric signal to feed a defect detecting signal to the sampling and holding means and to hold the floating threshold value in the sampling and holding means at the moment when the defect detecting signal is fed thereto, thereby adjusting the threshold value to the most suitable value in accordance with fluctuation of the reflected light; and selecting non-defective circular members from the defective ones upon completion of the inspection in response to said defect detecting signal;

whereby the surface defects can be optically inspected without touching the circular members.

9. A method according to claim 8, further comprising:

transmitting said defect detecting signals to a gate means;

passing clock pulses through the gate means in the absence of the defect detecting signals;

counting said clock pulses during a half cycle of the scanning; and processing the counted value to thereby detect the size of a surface of said circular member.

10. A method according to claim 9, further comprising:

counting said defect detecting signals during the half cycle of the scanning to thereby detect the number of surface defects on said circular member.

11. Apparatus for detecting an external defect of a circular member comprising:

a rotary stand rotatably mounted on a detecting table and placed thereon with the circular member to be rotated;

an automatic delivering means for delivering circular member to be inspected one after another to said rotary stand in a predetermined posture;

a slit light flux generating device for irradiating the slit light flux at an incidence angle large enough to cause regular light reflection to an upper surface of the circular member;

a photoelectric detector for receiving the regularly reflected light from the upper surface to convert same into electric signals;

a defect detecting circuit for continuously processing said electric signals of said photoelectric detector at least per full rotation of said rotary stand and detecting the external defects of the circular member, said defect detecting circuit comprising:

a low pass filter coupled to the output of the photoelectric detector to produce a filtered electric signal;

an attenuator to adjust the magnitude of the filtered electric signal and to feed a floating threshold value; and a comparator for comparing the output of the photoelectric detector with the floating threshold value; and a selecting mechanism for selecting non-defective circular members from defective ones upon completion of inspection in response to the defect detecting signals of said defect detecting circuit;

so that the surface defects can be optically inspected without touching the circular members.

12. Means for detecting an external defect of a circular member according to claim 11, wherein said scanning light source consists of a laser device.

13. Means for detecting an external defect of a circular member according to claim 11, wherein said slit light flux generating device includes:

a laser device;

a lens and mirror system for converting a laser beam into a slit light flux; and a slit section producing the slit light flux; and wherein said photoelectric detector includes:

a condenser receiving reflected rays from the upper surface of the circular member; and a photoelectric converter converting the received rays through said condenser into electric signals.

14. Apparatus for detecting an external defect of a circular member comprising:

a rotary stand rotatably mounted on a detecting table and placed thereon with the circular member to be rotated;

an automatical delivering mechanism for delivering circular members to be inspected one after another to the rotary stand in a predetermined posture;

a scanning light source for irradiating detecting rays, which are controlled and scanned at a speed faster than the rotating speed of the rotary stand substantially in parallel with a rotary axis of the rotary stand, to a conical surface of the circular member, said scanning light source comprising:

a laser radiating a monochromatic and directional beam;

a light deflector having a deflecting axis provided perpendicularly to the rotary axis of the rotary stand and polarizing and scanning said laser; and a projector lens projecting the deflected light sectorially scanned to conical surfaces as parallel rays;

a slit light flux generating device for irradiating a slit light flux to a radially outwardly projected portion of the circular member in the direction of the axis thereof as well as to an upper surface of the circular member at an incident angle large enough to cause regular light reflection, said slit light flux generating device comprising:

a laser device;

a lens and mirror system for converting a laser beam into a slit light flux;

a projector mirror irradiating the slit light flux to the projected portion of the circular member; and a slit section producing the slit light flux;

a first photoelectric detector for receiving a regularly reflected light conical surface to convert same into electric signals;

a photoelectric detecting array for receiving rays not interrupted by the projected portion to convert same into electric signals, said photoelectric detecting array forming a self scanning type photoelectric detecting array and comprising:

a diode array being arranged and provided in one line along the radial direction of the rotary stand; and a scanning circuit being connected to said diode array;

a projection detecting circuit for detecting a projection in accordance with the received rays in response to output of the photoelectric detecting array, said projection detecting circuit comprising:

a clock oscillator connected to the scanning circuit for successively scanning and driving the scanning circuit of the photoelectric detecting array;

a scanning start signal generator connected to the clock oscillator for triggering the scanning circuit to start scanning;

a signal generator for counting a scanning clock of the clock oscillator; and a comparator connected to the scanning circuit and the counter for detecting the projected portion based on a photoelectrically converting signal of the photoelectric detecting array and for supplying a projection detecting signal based on the counted value at such time when said counter stops counting by the projection detecting signal;

a second photoelectric detector for receiving a regularly reflected light from the upper surface to convert same into electric signals, said second photoelectric detector comprising:

a condenser receiving reflected rays from the upper surface of the circular member; and a photoelectric converter for converting the received rays through said condenser into electric signals;

first through third defect detecting circuits coninuously processing the electric signals of the first photoelectric detector, the projection detecting circuit and the second photoelectric detector at least per full rotation of the rotary stand and detecting the external defect of the circular member, said first defect detecting circuit comprising:

a delay circuit connected to the photoelectric detector for delaying an output of the photoelectric detector for a certain period of time;

an attenuator connected to the delay circuit for attenuating an output of said delay circuit;

an adder connected to the attenuator for adding a bias voltage to an output of said attenuator and feeding a floating threshold value;

a sample hold circuit connected to the adder for sample holding and feeding the floating threshold value; and a comparator connected to the photoelectric detector for comparing the output from said sample hold circuit with the output from the photoelectric detector to feed a defect detecting signal as well as holding the floating threshold value of said sample hold circuit by the defect detecting signal;

whereby said threshold value is adjusted to the most suitable value in accordance with the fluctuation of the reflected light; and a selecting mechanism for selecting non-defective circular members from defective one upon completion of inspection and in response to the defect detecting signals of the defect detecting circuit;

so that the surface defects can be optically inspected without touching the circular members.

* * * * *